(12) United States Patent
Haas et al.

(10) Patent No.: US 6,284,930 B1
(45) Date of Patent: Sep. 4, 2001

(54) PROCESS FOR THE PREPARATION OF 3-HYDROXYPROPANAL

(75) Inventors: Thomas Haas, Frankfurt; Liane Deusser, Erzhausen; Torsten Hahm, Hanau-Klein-Auheim; Willi Hofen, Rodenbach; Rudolf Vanheertum, Kahl, all of (DE)

(73) Assignee: E.I. Du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/382,998

(22) Filed: Aug. 25, 1999

Related U.S. Application Data

(60) Provisional application No. 60/146,421, filed on Jul. 30, 1999.

(51) Int. Cl.$^7$ .................................................. C07C 45/64
(52) U.S. Cl. ..................... 568/491; 568/458; 568/862; 568/895
(58) Field of Search .................. 568/458, 491, 568/862, 895

(56) References Cited

U.S. PATENT DOCUMENTS

| | | | |
|---|---|---|---|
| 4,331,800 | 5/1982 | Inata et al. | 528/289 |
| 5,015,789 | 5/1991 | Arntz et al. | 568/862 |
| 5,171,898 | 12/1992 | Arntz et al. | 568/862 |
| 5,276,201 | 1/1994 | Haas et al. | 568/491 |
| 5,284,979 | 2/1994 | Haas et al. | 568/491 |
| 5,334,778 | 8/1994 | Haas et al. | 568/862 |
| 5,364,984 | 11/1994 | Arntz et al. | 568/862 |
| 5,364,987 | 11/1994 | Haas et al. | 568/866 |
| 5,426,249 | 6/1995 | Haas et al. | 568/862 |
| 5,459,229 | 10/1995 | Kelsey et al. | 528/275 |
| 5,527,973 | 6/1996 | Kelsey | 568/862 |
| 5,594,092 | 1/1997 | Burkett et al. | 528/272 |
| 5,703,179 | 12/1997 | Asakura et al. | 526/59 |
| 5,869,191 | 2/1999 | Clemons Van Gaalen et al. | 428/482 |
| 5,895,807 | 4/1999 | Galko et al. | 525/444 |
| 5,962,745 | 10/1999 | Brossmer et al. | 568/491 |

FOREIGN PATENT DOCUMENTS

| | | | |
|---|---|---|---|
| 922166 | 1/1955 | (DE) | . |
| 23 41 000 | 7/1975 | (DE) | C08L/67/00 |
| 0 049 412 | 4/1985 | (EP) | D01F/6/92 |
| 547402 | 6/1993 | (EP) | . |
| 0713853 | 5/1996 | (EP) | C07C/45/64 |
| 857 709 | 8/1998 | (EP) | . |
| 1 016 692 A1 | 6/2000 | (EP) | D01F/6/84 |
| 1 016 741 A1 | 7/2000 | (EP) | D01F/6/62 |
| 51-143605 | 12/1976 | (JP) | . |
| 52-5320 | 1/1977 | (JP) | D01F/6/62 |
| 5-71013 | 3/1993 | (JP) | D01F/6/84 |
| 8-143502 | 6/1996 | (JP) | . |
| 11-61563 | 3/1999 | (JP) | D01F/6/84 |
| 11-286596 | 10/1999 | (JP) | C08L/67/02 |
| 95/10499 | 4/1995 | (WO) | C07C/51/09 |
| 98/49216 | 11/1998 | (WO) | C08G/63/78 |

OTHER PUBLICATIONS

W. G. Etzkorn et al., Acrolein and Derivatives, *Kirk–Othmer (4th Edition)*, 1, 232–251, 1991.

Traub, L.G., Synthesis and Textile Chemical Properties of Polytrimethyleneterephthalate, *Dissertation (English Translation)*, 1994.

Schauhoff, S. et al., New developments in the production of polytrimethylene terephthalate (PTT), *Man–Made Fiber Year Book*, Sep. 1996.

N. Yamashita, et al., "Polymerization of Acrolein by Several Cyclic Amines and Water System", *J. Macromol. Sci.–Chem.*, A7(2), pp. 569–571 (1973).

*Primary Examiner*—Sreeni Padmanabhan

(57) ABSTRACT

3-Hydroxypropanal is prepared by reacting acrolein with water under pressure and in the presence of an ion exchange resin while adding a carboxylic acid to the reaction mixture.

26 Claims, No Drawings

PROCESS FOR THE PREPARATION OF 3-HYDROXYPROPANAL

This application claims priority benefit of Provisional Application 60/146,421, filed Jul. 30, 1999.

FIELD OF THE INVENTION

The invention concerns a process for the preparation of 3-hydroxypropanal.

TECHNICAL BACKGROUND

3-Hydroxypropanal is an intermediate product in the preparation of 1,3-propane diol. 1,3-Propane diol may be further processed to form polyesters, for example poly (trimethylene terephthalate), which is useful for the spinning of fibers, or may be processed to other articles of commerce such as polyols.

It is known that 3-hydroxypropionaldehyde (3-hydroxypropanal) can be prepared by hydration of acrolein with water in the presence of a chelate-forming ion exchanger at temperatures of 30 to 120° C. and pressures of 1 to 20 bars as described in U.S. Pat. No. 5,171,898, herein incorporated by reference.

U.S. Pat. No. 5,284,979 discloses the hydration of 2-alkenals to 3-hydroxyalkanals in a homogeneous phase in the presence of an acid catalyst and a dissolved acid-base buffer which results in a pH of from 2 to 5. A preferred acid base buffer is propanoic acid/triethyl ammonium propionate.

EP 0713853 discloses the addition of oxalic acid to a process for the hydration of acrolein to 3-hydroxypropanal in the presence of a lead-containing ion exchange resin.

Japanese Patent application Kokai No. H 8-143502 discloses the preparation of 3-hydroxyalkanals by the hydration of unsaturated aldehydes in the presence of a metal-carrying ion-exchange resin with the addition of a carboxylic acid to the reaction mixture. Mono and polycarboxylic acids are broadly disclosed, a dicarboxylic acid such as oxalic acid is especially preferred.

The known processes have the disadvantage that the catalysts used do not exhibit life times as long as desired. Life time is impaired because of depositions of acrolein polymers on the ion exchanger bed occurring over the course of operation. The acrolein polymers create an increase in pressure differential across the ion exchanger bed and hence a drop in conversion of the unsaturated aldehyde. The ion exchanger must, therefore, be renewed periodically after undesirably short periods of time.

Achievement of economic continuous operation, however, requires an adequately long life time. An object of this invention, therefore, is to improve the known process for the preparation of 3-hydroxypropanal by providing adequately long catalyst life times.

SUMMARY OF THE INVENTION

The present invention is a process for the preparation of 3-hydroxypropanal by hydration of acrolein in the presence of an ion exchange resin, wherein acrolein and water are reacted in the weight ratio of 1:2 to 1:20, at 30 to 120° C. and at a pressure in the range of 1 to 20 bar, using a chelate-forming ion exchanger which contains, bound to the polymer matrix of the polymeric resin, anchor groups of the general formula

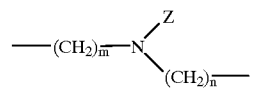

wherein
Z is H, $C_1$–$C_6$ alkyl, —$CH_2$—$CH(CH_3)$—Y' or —$(CH_2)_o$—Y',
Y and Y' are equal or different: —COOH, —OH, pyridyl, or $P(O)(OH)_2$, wherein the acidic functional groups may be present, in part, in the form of their salts with alkali, alkaline earth or earth metals,
m is 0, 1, 2 or 3,
n is 1, 2 or 3 for Y=—COOH, pyridyl or —$P(O)(OH)_2$; 2 or 3 for Y=OH, o is 1, 2 or 3 for Y'=COOH, pyridyl or —$P(O)(OH)_2$; 0, 2 or 3 for Y'=—OH,
said process being characterized in that a carboxylic acid is added to the reaction mixture.

The amount of carboxylic acid can be from 1 ppm to 50,000 ppm, preferably 10 ppm to 5,000 ppm by weight in the reaction mixture.

The process of the invention has the advantage that the addition of propanoic acid prevents an increase in the pressure differential in the reactor. Drop-off in conversion in the reactor is reduced significantly. Both these effects produce a distinctly longer life time for the catalyst.

DETAILED DESCRIPTION OF THE INVENTION

In carrying out the invention acrolein and water are supplied in a weight ratio of 1:2 to 1:20, especially 1:3 to 1:10 and preferably 1:3 to 1:6 to the hydration stage. The conversion to 3-hydroxypropionaldehyde takes place in a temperature range of 30° C. to 120° C. A temperature in a range of 40 to 90° C. is preferred; a temperature below 40° C. generally results in longer reaction times whereas a temperature above 90° C. results in a reduced selectivity and problems regarding the service life of the exchange resins. It is especially preferred if the hydration takes place at 50° C. to 80° C.

The amount of the carboxylic acid in the hydration reaction mixture can be from 1 ppm to 50,000 ppm, preferably 10 ppm to 5,000 ppm. An amount of carboxylic acid is used to maintain the pH of the reaction mixture in the range of from 1 to 5.5, preferably in the range of from 4 to 5.

Preferred carboxylic acids are aliphatic carboxylic acids containing from 2 to 8 carbon atoms. Especially preferred carboxylic acids are propenoic acid and propanoic acid. Most preferred is propanoic acid.

In the temperature range below the boiling point of acrolein, the reaction can take place at normal pressure or at moderate pressure. In the case of reaction temperatures around or above the boiling point of acrolein, the work is performed under a pressure in a range of approximately 2 to 20 bars. In the preferred temperature range of 40 to 90° C., a pressure in a range of 2 to 5 bars is preferred.

The hydration is generally carried out up to an acrolein conversion in a range of 30 to 90% or above; a conversion of 40 to 90% and especially 50 to 80% is preferred.

The hydration can take place either discontinuously or continuously and known reactors such as agitator reactors, loop reactors, floating bed reactors, fluid bed reactors and fixed bed reactors can be used. The last-named reactors are preferred over loop reactors and agitator reactors. The residence time and temperature in a fixed bed reactor containing a chelate-forming ion exchanger are controlled in such a manner that the desired acrolein conversion is achieved with a single passage of the reaction mixture through the reactor.

After separation of the ion exchanger, which usually takes place by means of sedimentation or filtration or results by itself when using a resin bed (as is customary, for example, in softened water preparation), the reaction mixture is freed, to the extent necessary, of non-reacted acrolein. The separation of the acrolein can be realized in a known manner, especially by means of distillation, preferably under reduced pressure and temperatures below 80° C. The recovered acrolein can be fed back into the process after stabilization. The practically acrolein-free hydroxypropionaldehyde solution obtained can be reconcentrated before hydrogenation e.g., via a thin-layer evaporator.

A special advantage of the use of propanoic acid as the carboxylic acid in the process of the present invention is the fact that propanoic acid can be removed from the hydrated reaction mixture as an azeotrope with water and thus is not carried downstream to the subsequent (hydrogenation) stage.

As used herein, the term "earth metal" is intended to designate the elements Al, Sc, Y, La and the 14 lanthanides; see Roempps Chemie-Lexikon.

Experiments to demonstrate the reaction of acrolein to 3-hydroxypropanal are performed in a tubular apparatus under continuous flow. The reactor consists of a double-jacketed glass tube of 3 m length and 76 mm inner diameter. The reactor is charged with ion exchanger Lewatit TP 208 (acid form) as obtained from Bayer AG. The aqueous solution is preheated to reaction temperature and pumped through the catalyst bed from the bottom up. The reactor is maintained at temperature by a thermostat. A pressure of 2.5 bar absolute is set on the exit of the reactor. Both feed and product solutions are analyzed by gas chromatography. Analyses are then used to determine conversion and selectivity of the reaction. The product solution is then hydrogenated according to the procedure of U.S. Pat. No. 5,334,778 and the hydrogenation product is distilled. After completing distillation, the content of propanoic acid in the H$_2$O-distillate and the purity of 1,3-propanediol in the 1,3-propanediol distillate were determined by gas chromatography.

COMPARATIVE EXAMPLE 1

The reactor tube was charged with 10.5 l ion exchanger. An aqueous acrolein solution at a concentration of 17.5 wt. % was pumped through the ion exchanger, at a volume flow of 6.5 l/hour. The average reactor temperature was 69° C. The pH-value of the solution was 5.8 prior to exposure to the ion exchanger. After an experimental duration of about 10 hours, the measured pressure differential across the reactor was 0.4 bar. Conversion was 54.5 % and selectivity was 81.8%. After an additional interval of 144 hours, the pressure differential was 0.8 bar, conversion was 49.3% and selectivity 81.6%. No propanoic acid was detected in the H$_2$O-distillate. Purity of the 1,3-propane diol distillate was 99.7 GC-area %.

EXAMPLE 1

The reactor tube was charged with 10.5 l catalyst. Acrolein concentration in the aqueous solution was 17.5% and 100 ppm of propanoic acid was added. The solution was pumped through the catalyst bed at a rate of 6.5 l/hour. Average reactor temperature was 69° C. and the pH value ahead of the reactor was 4.1. After an experimental duration of about 10 hours, pressure differential on the reactor of 0.4 bar was reached. Conversion was 54.4%, and the selectivity with respect to 3-hydroxypropanal was 81.9%. After an additional interval of 316 hours, the pressure differential was measured at 0.4 bar, conversion was 53.9 % and selectivity with respect to 3-hydroxypropanal was 81.4%. Eighty percent of the propanoic acid charged was found in the H$_2$O-distillate. Purity of the 1,3-propane diol distillate was 99.8 GC-area %.

When Comparison Example 1 and Example 1 are compared, it is evident that the addition of propanoic acid prevents an increase in reactor pressure differential and also significantly reduces the drop in conversion in the reactor with extended reaction times. Both lead to significantly prolonged catalyst life time.

We claim:
1. A process for the preparation of 3-hydroxypropanal by hydration of acrolein in the presence of an ion exchanger, wherein acrolein and water are reacted in a weight ratio of 1:2 to 1:20, at 30° C. to 120° C. and at a pressure in the range of 1 to 20 bar, using a chelate-forming ion exchanger which contains, bound to a polymer matrix of a polymeric resin, anchor groups of the general formula

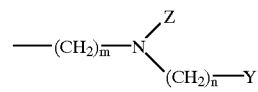

wherein
Z is H, C$_1$–C$_6$ alkyl, —(CH$_2$—CH(CH$_3$)—Y' or —(CH$_2$)$_o$—Y',
Y and Y', which are the same or different, are —COOH, —OH, pyridyl or —P(O)(OH)$_2$, wherein the acidic functional groups may be present, in part, in the form of their salts with alkali, alkali earth or earth metals,
m is 0, 1, 2 or 3,
n is 1, 2 or 3 for Y=—COOH, pyridyl or —P(O)(OH)$_2$; 2 or 3 for Y=—OH,
o is 1, 2 or 3 for Y'—COOH, pyridyl or —P(O)(OH)$_2$; 0, 2 or 3 for Y'=—OH, said process comprising adding a carboxylic acid to the reaction mixture.
2. The process of claim 1 wherein the amount of carboxylic acid in the reaction mixture is from 1 ppm to 50,000 ppm by weight.
3. The process of claim 2 wherein the amount of carboxylic acid in the a reactant mixture is from 10 ppm to 5,000 ppm by weight.
4. The process of claim 1 wherein the carboxylic acid is added in amount so that pH of the reaction mixture is from 1 to 5.5.
5. The process of claim 4 wherein the carboxylic acid is added in amount so that pH of the reaction mixture is from 4 to 5.
6. The process of claim 1 wherein the carboxylic acid is an aliphatic carboxylic acid containing from 3 to 8 carbon atoms.
7. The process of claim 6 wherein the carboxylic acid is selected from the group consisting of propenoic acid and propanoic acid.
8. The process of claim 7 wherein the carboxylic acid is propanoic acid.
9. The process of claim 1 wherein the hydration is carried out in a reactor selected from the group consisting of agitator reactors, loop reactors, floating bed reactors, fluid bed reactors and fixed bed reactors.

10. The process of claim 1 wherein the hydration is carried out in a reactor selected from the group consisting of floating bed reactors, fluid bed reactors and fixed bed reactors.

11. The process of claim 1 wherein the hydration is carried out in a single pass through a fixed bed reactor containing the chelate-forming ion exchanger.

12. The process of claim 1 wherein the carboxylic acid is removed from the reaction mixture as an azeotrope with water.

13. The process of claim 1, wherein hydration is carried out up to an acrolein conversion of 30 to 90 percent and non-reacted acrolein is separated by distillation.

14. The process of claim 13 when the acrolein separated by the distillation is stabilized and fed back into the reaction mixture.

15. A process for the preparation of 3-hydroxypropanal by hydration of acrolein in the presence of an ion exchanger, wherein acrolein and water are reacted in a weight ratio of 1:2 to 1:20, at 30° C. to 120° C. and at a pressure in the range of 1 to 20 bar, using a chelate-forming ion exchanger, wherein the chelate-forming ion exchanger contains, bound to a polymer matrix of a polymeric resin, anchor groups of the general formula

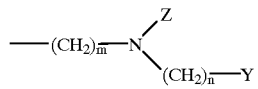

wherein

Z is H, $C_1$–$C_6$ alkyl, —($CH_2$—CH($CH_3$)—Y' or —($CH_2$)$_o$—Y',

Y and Y', which are the same or different, are —COOH, —OH, pyridyl or —P(O)(OH)$_2$, wherein the acidic functional groups may be present, in part, in the form of their salts with alkali, alkaline earth or earth metals, m is 0, 1, 2 or 3, n is 1, 2 or 3 for Y═—COOH, pyridyl or —P(O)(OH)$_2$; 2 or 3 for Y═—OH, o is 1, 2 or 3 for Y'—COOH, pyridyl or —P(O)(OH)$_2$; 0, 2 or 3 for Y'═—OH, further comprising adding an additive consisting essentially of a carboxylic acid.

16. The process of claim 15 wherein the amount of carboxylic acid in the reaction mixture is from 1 ppm to 50,000 ppm by weight.

17. The process of claim 16 wherein the amount of carboxylic acid in the reactant mixture is from 10 ppm to 5,000 ppm by weight.

18. The process of claim 15 wherein the carboxylic acid is added in amount so that pH of the reaction mixture is from 1 to 5.5.

19. The process of claim 16 wherein the carboxylic acid is added in amount so that pH of the reaction mixture is from 4 to 5.

20. The process of claim 15 wherein the carboxylic acid is an aliphatic carboxylic acid containing from 3 to 8 carbon atoms.

21. The process of claim 20 wherein the carboxylic acid is selected from the group consisting of propenoic acid and propanoic acid.

22. The process of claim 19 wherein the carboxylic acid is propanoic acid.

23. The process of claim 1 wherein the ion exchanger acts as a catalyst for the hydration and the carboxylic acid prolongs the life of the catalyst.

24. The process of claim 15 wherein the ion exchanger acts as a catalyst for the hydration and the carboxylic acid of the additive prolongs the life of the catalyst.

25. The process of claim 23 wherein the reaction is carried out in a reactor and the carboxylic acid prolongs the life of the catalyst by preventing an increase in the reactor pressure differential and reducing the drop in conversion in the reactor with extended reaction times.

26. The process of claim 15 wherein the process consists essentially of treating the reaction mixture with the additive.

* * * * *